United States Patent
Kergosien et al.

(10) Patent No.: US 9,962,327 B2
(45) Date of Patent: May 8, 2018

(54) COSMETIC COMPOSITION COMPRISING AT LEAST ONE ALKOXYSILANE

(71) Applicant: L'OREAL, Paris (FR)

(72) Inventors: Guillaume Kergosien, Chaville (FR); Carl Riachi, Paris (FR); Laure Le Chaux, L'Hay-les-Roses (FR)

(73) Assignee: L'OREAL, Paris (FR)

( * ) Notice: Subject to any disclaimer, the term of this patent is extended or adjusted under 35 U.S.C. 154(b) by 3 days.

(21) Appl. No.: 14/357,409

(22) PCT Filed: Nov. 9, 2012

(86) PCT No.: PCT/IB2012/056925
§ 371 (c)(1),
(2) Date: May 9, 2014

(87) PCT Pub. No.: WO2013/068979
PCT Pub. Date: May 16, 2013

(65) Prior Publication Data
US 2014/0314696 A1    Oct. 23, 2014

Related U.S. Application Data

(60) Provisional application No. 61/565,519, filed on Dec. 1, 2011.

(30) Foreign Application Priority Data

Nov. 9, 2011 (FR) .................................. 11 60212

(51) Int. Cl.
*A61Q 1/04* (2006.01)
*A61Q 3/02* (2006.01)
*A61Q 5/00* (2006.01)
*A61Q 1/06* (2006.01)
*A61K 8/58* (2006.01)
*A61K 8/73* (2006.01)
*A61Q 1/00* (2006.01)

(52) U.S. Cl.
CPC ............ *A61K 8/585* (2013.01); *A61K 8/731* (2013.01); *A61Q 1/00* (2013.01); *A61Q 1/04* (2013.01); *A61Q 1/06* (2013.01); *A61Q 3/02* (2013.01); *A61Q 5/00* (2013.01); *A61K 2800/882* (2013.01); *A61K 2800/94* (2013.01)

(58) Field of Classification Search
None
See application file for complete search history.

(56) References Cited

U.S. PATENT DOCUMENTS

| 6,852,300 | B2* | 2/2005 | Costa ................. C03C 1/008 |
| | | | 423/326 |
| 2002/0041856 | A1 | 4/2002 | Jeanne-Rose et al. |
| 2004/0166075 | A1 | 8/2004 | Jeanne-Rose et al. |
| 2006/0110351 | A1* | 5/2006 | Koehler et al. ............ 424/70.12 |
| 2008/0089917 | A1* | 4/2008 | Dumousseaux ......... A61K 8/25 |
| | | | 424/401 |

FOREIGN PATENT DOCUMENTS

| EP | 1 172 079 | 1/2002 |
| EP | 1 767 187 | 3/2007 |
| JP | 09-309717 | * 12/1997 |
| JP | 2002-97114 A | 4/2002 |
| JP | 2002-529383 A | 9/2002 |
| JP | 2004-519429 A | 7/2004 |
| JP | 2009-57339 A | 3/2009 |
| WO | 2012/038880 | 3/2012 |

OTHER PUBLICATIONS

International Search Report dated Jan. 27, 2014, in PCT/IB12/056295, filed Nov. 9, 2012.
French Search Report dated Oct. 9, 2012 in Application No. FR 1160212 filed Nov. 9, 2011(with English translation).
Written Opinion of the International Searching Authority dated Jan. 27, 2014, in PCT/IB12/056295, filed Nov. 9, 2012.
Office Action dated Aug. 29, 2016 in Japanese Patent Application No. 2014-540622 (with English translation).

* cited by examiner

*Primary Examiner* — Jyothsna A Venkat
(74) *Attorney, Agent, or Firm* — Oblon, McClelland, Maier & Neustadt, L.L.P.

(57) ABSTRACT

The present invention relates to a cosmetic or dermatological composition of sol/gel type for making up and/or caring for keratin materials characterized in that it comprises the product resulting from the reaction: (a) of at least one alkoxysilane monomer or oligomer of formula (I) $R1_xSi(OR2)_{(4-x)}$ or of formula (II) $[R1_y(OR2)_z SiO_{((4-y-z)/2)}]_\eta$ in which R1 represents, independently, a nucleophilic group other than a hydroxyl, or a (Ci-C2o)alkyl group, R2 represents, independently, a (Ci-Cio)alkyl group, and (b) of an amount of water corresponding to a number of moles of water, determined according to the following equation: $X=(\text{nAlkoxysilanes} \times \text{nbAlkoxy groups})/n_{H2o}$ with $n_{H2o}$=Number of moles of water, nAikoxysiianes=Number of moles of alkoxysilane compounds, nbAikoxy groups=Weighted mean of the number of alkoxysilane groups per alkoxysilane compound, and X is a number greater than 2. It also relates to an associated cosmetic process and an associated kit for coating keratin materials.

6 Claims, No Drawings

COSMETIC COMPOSITION COMPRISING AT LEAST ONE ALKOXYSILANE

A subject of the present invention is a cosmetic or dermatological composition of sol/gel type for making up and/or caring for keratin materials.

This composition is obtained by sol/gel reaction by mixing at least one alkoxysilane and at least one specific amount of water, determined according to the number of moles of alkoxy groups in the mixture.

The present invention is more particularly directed towards a nail varnish, in particular a long-lasting nail varnish.

Compositions have already been described which comprise gels based on alkoxysilanes comprising at least one odorous substance, in particular in application FR 2 913 887.

The use of sol/gel techniques for the purposes of preparing a cosmetic composition is also known per se. Mention may in particular be made of documents EP 1 172 079, GB 2 403 406 or else US 2010/0226869, which mention combinations of silicone resins useful for the formation of silicone films in the cosmetic field.

It has never been demonstrated in any of these documents that the amount of water has an influence on the properties of the composition before formation of the gel, in particular, in terms of stability.

However, it has been noted that the use of these resins can prove to be tricky since unwanted gelling of the liquid composition comprising the oligomers can occur before application to keratin materials. Indeed, in the context of the present invention, the objective is more particularly to obtain the formation of a film which is long-lasting after application to keratin materials. During drying, a material in fact forms by polycondensation and cross-linking on the nanometer scale.

There is consequently a need to provide compositions carrying out sol/gel reactions based on alkoxysilane compounds which exhibit both good reactivity and properties of stability before application thereof to keratin materials.

There is also a need to provide compositions carrying out sol/gel reactions based on alkoxysilane compounds capable of forming films or coatings which are long-lasting.

Rapid drying of the film or coating obtained is also sought.

Specifically, the layer of the composition deposited on the keratin materials may, if the reaction takes place slowly and if it does not dry quickly, prove to be tacky after its application and/or to be degraded on contact with foreign bodies with which it may come into contact, for instance a glass, a cigarette, an item of clothing or the skin, which will be an inconvenience to users.

Finally, properties of persistence on washing with water and with detergents are sought.

The inventors have noted that such advantages can be obtained by using particular alkoxysilane monomers or oligomers, in the presence of a specific amount of water, in particular related to the number of moles of alkoxy groups resulting from the alkoxysilane monomers or oligomers.

They have thus been able to note, as reported in the examples hereinafter, that, beyond a certain amount of water in the cosmetic composition, still in this ratio with respect to the number of moles of alkoxy groups resulting from the alkoxysilane monomers or oligomers, the desired properties in terms of stability over time are not satisfactorily provided.

Thus, the subject of the present invention is a cosmetic or dermatological composition of sol/gel type for making up and/or caring for keratin materials characterized in that it comprises the product resulting from the reaction:

(a) of at least one alkoxysilane monomer or oligomer of formula (I) $R^1_x Si(OR^2)_{(4-x)}$ or of formula (II) $[R^1_y (OR^2)_z SiO_{((4-y-z)/2)}]_n$ in which:

$R^1$ represents, independently, a nucleophilic group other than a hydroxyl, or a $(C_1-C_{20})$alkyl group, optionally substituted with at least one nucleophilic group, with at least one of the $R^1$ groups of said monomer or oligomer being a nucleophilic group or a $(C_1-C_{20})$alkyl group substituted with at least one nucleophilic group, $R^2$ represents, independently, a $(C_1-C_{10})$alkyl group, x represents 1, 2 or 3, y represents, independently, 1 or 2, z represents, independently, 0, 1 or 2, the sum of y and z being less than or equal to 3, n represents an integer between 2 and 1000, and (b) of an amount of water corresponding to a number of moles of water, determined according to the following equation:

$$X = (n_{Alkoxysilanes} \times nb_{Alkoxy\ groups})/n_{H2O}$$

with:

$n_{H2O}$=Number of moles of water, $n_{Alkoxysilanes}$=Number of moles of alkoxysilane compounds, $nb_{Alkoxy\ groups}$=Weighted mean of the number of alkoxysilane groups per alkoxysilane compound, and X is a number greater than 2, in particular between 2 and 500.

The term "weighted mean" is intended to mean:

the number of alkoxy groups per alkoxysilane molecule, when a single alkoxysilane compound is present in the composition, the mean weighted by the molar ratio of the number of alkoxy groups per alkoxysilane molecule, when several alkoxysilane compounds (A1, A2, etc.) are present in the composition.

The selection of such an amount of water makes it possible to hydrolyze only a part of the alkoxysilane monomers or oligomers of the composition. Thus, the gelling is delayed until the moment of application to the keratin materials, and the stability over time of the composition is thus improved.

The number of moles of silicon of the alkoxysilane monomers and oligomers is to be taken into consideration on the basis of all of said alkoxysilane monomers and oligomers, namely corresponding to (a) defined above or any other additional alkoxysilane monomer or oligomer.

The present invention also relates to a kit for coating keratin materials and/or the teeth, comprising at least one product resulting from the reaction of (a) and (b) as defined above, and to a cosmetic process for coating keratin materials using a cosmetic composition according to the present invention or said kit.

A cosmetic composition according to the present invention is liquid.

In the context of the present invention, the term "liquid composition" is intended to mean a composition which has a particular viscosity at ambient temperature, namely 20° C.

More specifically, a liquid composition has, at 20° C., a viscosity ranging from 0.001 to 20 Pa/s, preferably from 0.01 to 10 Pa/s and even more preferably from 0.1 to 2 Pa/s.

The viscosity measurement can be carried out at 20° C. using a Rheomat RM 180 viscometer equipped with a No. 4 rotor, the measurement being performed after 10 minutes of rotation of the rotor in the composition (after which time stabilization of the viscosity and of the spin speed are observed), at a shear rate of 200 s$^{-1}$.

In the context of the present invention, the term "alkoxysilane" is intended to mean a compound comprising at least one silicon atom bearing at least one alkoxy group.

The expression "property of stability before application" is intended to mean the ability to remain in liquid form, i.e. not to gel, before application to the keratin materials.

The term "between" is intended to mean inclusively between.

Preferably, the expression "ability to remain in liquid form" is intended to mean the ability of the composition to remain in liquid form after one week of storage at 60° C.

Cosmetic Composition

According to one particular embodiment, the amount of water present in the reaction medium which makes it possible to obtain the product included in the composition according to the present invention corresponds to a number of moles of water determined according to the following equation:

$$X = (n_{Alkoxysilanes} \times nb_{Alkoxy\ groups})/n_{H2O}$$

with:
- $n_{H2O}$=Number of moles of water,
- $n_{Alkoxysilanes}$=Number of moles of alkoxysilane compounds,
- $nb_{Alkoxy\ groups}$=Weighted mean of the number of alkoxysilane groups per alkoxysilane compound,
- X is a number between 2 and 500, preferentially between 2.5 and 500, and even more preferentially X is between 3 and 500.

According to one particular embodiment, X is equal to 2 or 2.5 or else 3.

Indeed, the higher the value of X, the higher the crosslinking potential. Thus, a high X further improves the stability.

According to one particular embodiment of the invention, the alkoxysilane monomer of formula $R^1_xSi(OR^2)_{(4-x)}$ (I) can be chosen from the compounds of formulae (Ia) et (Ib) below

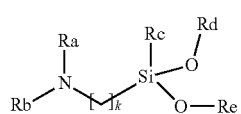
(Ia)

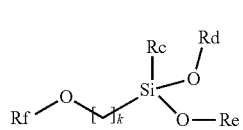
(Ib)

in which:
Ra et Rb represent, independently, a hydrogen atom or a ($C_1$-$C_{20}$)alkyl group, such as a methyl group or a cyclohexyl group, or an aryl group, such as a phenyl or a benzyl, or a ($C_1$-$C_{20}$)aminoalkyl group, or a ($C_1$-$C_{20}$) hydroxyalkyl group, or a ($C_1$-$C_{10}$)alkoxy group, or a group of formula (III) or (IV) below:

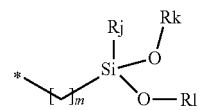
(III)

with Rj representing a ($C_1$-$C_{20}$)alkyl group such as a methyl or a ($C_1$-$C_{10}$)alkoxy group, preferably an ethoxy group, with Rk et Rl, independently, representing a ($C_1$-$C_{10}$)alkyl group, preferably an ethyl group,

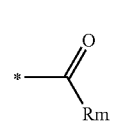
(IV)

with Rm representing a ($C_1$-$C_{20}$)alkyl group or a ($C_1$-$C_{10}$) alkoxy group, such as a methoxy, or an amino group, Ra and Rb possibly being connected so as to form a ring, for example a piperidyl group, Rc represents, independently, a ($C_1$-$C_{20}$)alkyl group such as a methyl or a ($C_1$-$C_{10}$)alkoxy group, preferably an ethoxy group, Rd and Re, independently, represent a ($C_1$-$C_{10}$)alkyl group, preferably an ethyl group, Rf represents a hydrogen atom or a ($C_1$-$C_{20}$)alkyl group, or a group of formula (V) below:

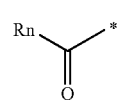
(V)

with Rn representing a ($C_1$-$C_{20}$)alkyl group, preferably a methyl group, k and m represent, independently, an integer between 1 and 20, preferably between 1 and 3, preferably equal to 1.

In the context of the present invention, the term:
- <<($C_1$-$C_{20}$)alkyl>> denotes a linear or branched, and saturated or unsaturated, hydrocarbon-based chain containing from 1 to 20 carbon atoms. Mention may in particular be made of methyl, ethyl, 1-propyl and 2-propyl groups,
- <<($C_1$-$C_{10}$)alkoxy>> denotes an —O—($C_1$-$C_{10}$)alkyl group. Mention may in particular be made of methoxy, ethoxy, 1-propoxy and 2-propoxy groups,
- "aryl" denotes an aromatic group containing from 5 to 14 carbon atoms. Mention may in particular be made of the benzyl group or the phenyl group.

In the context of the present invention, a nucleophilic group is intended to mean preferably an amino or thiol group, and even more preferably an amino group.

By way of amino group, mention may in particular be made of the aminopropyl or N-cyclohexylaminomethyl group.

According to one particular embodiment of the invention, the cosmetic composition comprises at least one compound of formula (Ia) as defined above, as compound of formula (I).

Among the alkoxysilane compounds of formula (Ia), mention may in particular be made of 3-aminopropyltriethoxysilane (APTES), 3-aminopropylmethyldiethoxysilane (APMDES) and the oligomers formed from APTES or from APMDES or else N-cyclohexylaminomethyltriethoxysilane.

The APTES may, for example, be sold by the company Dow Corning under the name Xiameter OFS-6011 Silane or under the name APTES Silsoft A-1100 by the company Momentive Performance Materials.

APMDES may be sold, for example, by the company Evonik under the name Dynasylan 1505.

The N-cyclohexylaminomethyltriethoxysilane may be sold, for example, by the company Wacker under the name Geniosil XL 926.

Preferentially, the alkoxysilane compound comprising at least one nucleophilic group is 3-aminopropyltriethoxysilane (APTES).

According to one particular embodiment, the composition can contain at least one additional alkoxysilane chosen from the compounds of formulae $Si(OR^{2'})_4$; $R^3{}_xSi(OR^{2'})_{(4-x')}$ and $[R^3{}_{y'}(OR^{2'})_zSiO_{((4-y'-z')/2)}]_{n'}$, in which:
R³ represents, independently:
a ($C_1$-$C_{20}$)alkyl group, which can be optionally substituted with a (meth)acrylate group, an acetoxy group or a glycidoxy group,
an aryl group, such as a phenyl or benzyl group, or
a fluoroalkyl group such as the tridecafluorooctyl group,
R² represents, independently, a hydrogen atom or a ($C_1$-$C_{10}$)alkyl group,
x' represents 1, 2, or 3,
y' represents, independently, 0, 1 or 2,
z' represents, independently, 0, 1, 2 or 3,
the sum of y' and z' being less than or equal to 3,
n' represents an integer between 2 and 1000.

Still in the context of this particular embodiment, the additional alkoxysilane can be chosen preferably from tetraethoxysilane (TEOS), methyltriethoxysilane (MTES), dimethyldiethoxysilane (DMDES), diethyldiethoxysilane, dipropyldiethoxysilane, propyltriethoxysilane, isobutyltriethoxysilane, phenyltriethoxysilane, phenylmethyldiethoxysilane, diphenyldiethoxysilane, benzyltriethoxysilane, benzylmethyldiethoxysilane, dibenzyldiethoxysilane, acetoxymethyltriethoxysilane and mixtures thereof.

The acetoxymethyltriethoxysilane may be sold, for example, by the company ABCR under the name AB 110784.

According to an even more particular embodiment, the present invention relates to a cosmetic or dermatological composition of sol/gel type for making up and/or caring for keratin materials, and/or for making up the teeth, characterized in that it comprises a product resulting from a reaction of (a) and (b) and optionally (c), (d), (e), (f) and/or (g) as defined hereinafter:

a) at least one alkoxysilane monomer chosen from the compounds of formulae (Ia) and (Ib) below;

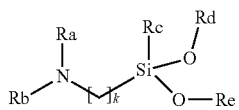

(Ia)

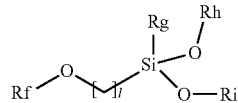

(Ib)

as defined above; and (b) an amount of water corresponding to a number of moles of water, which can be determined according to the following equation:

$$X = (n_{Alkoxysilanes} \times nb_{Alkoxy\ groups})/n_{H2O}$$

with:
$n_{H2O}$=Number of moles of water,
$n_{Alkoxysilanes}$=Number of moles of alkoxysilane compounds,
$nb_{Alkoxy\ groups}$=Weighted mean of the number of alkoxysilane groups per alkoxysilane compound, and
X is a number between 2 and 500, preferentially between 2.5 and 500, and even more preferentially X is between 3 and 500, (c) an acid and/or a base, for example as defined hereinafter;

(d) at least one alkoxysilane chosen from the compounds of formulae $Si(OR^{2'})_4$; $R^3{}_xSi(OR^{2'})_{(4-x')}$ and $[R^3{}_{y'}(OR^{2'})_zSiO_{((4-y'-z')/2)}]_{n'}$, in which:
R³ represents, independently:
a ($C_1$-$C_{20}$)alkyl group, which can be optionally substituted with a (meth)acrylate group or a glycidoxy group,
an aryl group, such as a phenyl or benzyl group, or
a fluoroalkyl group such as the tridecafluorooctyl group,
R²' represents, independently, a hydrogen atom or a ($C_1$-$C_{10}$)alkyl group,
x' represents 1 or 2,
y' represents, independently, 0, 1 or 2,
z' represents, independently, 0, 1, 2 or 3,
the sum of y' and z' being less than or equal to 3,
n' represents an integer between 2 and 1000;

(e) at least one film-forming polymer as described hereinafter, preferably a cellulose derivative, such as ethylcellulose or cellulose acetobutyrate, preferably a silicone resin, such as polysilsesquioxanes;

(f) at least one additive comprising a hydroxyl function as described hereinafter, preferably glycols, such as glycerol; and (g) at least one solvent or a mixture of solvents, such as alcohol or an acetate described hereinafter.

Preferably, the composition comprises more than 25%, even more preferentially more than 50% by weight of the sum of the product resulting from the reaction of (a) and (b) and of the compounds (c) and (d), relative to the total weight of the composition.

According to one particular embodiment, R³ of said alcoxysilane (d) represents, independently, a ($C_1$-$C_{20}$)alkyl group or an aryl group, such as a phenyl or benzyl group.

According to another particular embodiment, the alkoxysilane (d) is chosen from tetraethoxysilane (TEOS), methyltriethoxysilane (MTES), dimethyldiethoxysilane (DMDES), diethyldiethoxysilane, dipropyldiethoxysilane, propyltriethoxysilane, isobutyltriethoxysilane, phenyltriethoxysilane, phenylmethyldiethoxysilane, diphenyldiethoxysilane, benzyltriethoxysilane, benzylmethyldiethoxysilane, dibenzyldiethoxysilane, and mixtures thereof.

The TEOS may be sold, for example, under the name Dynasylan TEOS UHP by the company Evonik.

The MTES may be sold, for example, by the company Evonik under the name Dynasylan MTES.

According to one particular embodiment of the invention, the alcohol generated in the composition during the hydrolysis and condensation reaction can be partially or totally removed, in particular by evaporation under vacuum.

According to yet another embodiment, the composition can comprise a solvent or a mixture of solvents.

Acid

A composition according to the present invention can also comprise at least one acid.

This acid may be chosen from lactic acid, acetic acid, citric acid, tartaric acid, hydrochloric acid, sulfuric acid and phosphoric acid.

This acid is preferably hydrochloric acid.

The hydrochloric acid (pure) may in particular be present in the composition in a content of between 0.001% and 0.1% by weight and preferably in a content of between 0.01% and 0.05% by weight relative to the total weight of the composition.

Additional Compounds

A composition according to the invention may also comprise at least one polar volatile solvent.

The term "polar volatile solvent" denotes, in the present invention, a compound which is liquid at ambient temperature, which comprises at least one polar group such as a hydroxyl, ester, ketone, ether or aldehyde group, and which has a vapour pressure greater than 1 mbar at 20° C.

Among the polar volatile solvents which can be used in the compositions in accordance with the invention, mention may in particular be made of $C_1$-$C_5$ monoalcohols preferably chosen from ethanol, isopropanol, butanol, butan-2-ol, methylpropan-1-ol and methylpropan-2-ol, and preferably ethanol. Mention may also be made of $C_3$-$C_4$ ketones, $C_2$-$C_4$ aldehydes, and $C_2$-$C_4$ short-chain esters, preferably chosen from ethyl acetate, propyl acetate and butyl acetate.

Such a polar volatile solvent may be present in the composition in a concentration of greater than 10% by weight relative to the total weight of the composition.

Preferably, the polar volatile solvent is present in the composition at a concentration of greater than 20% by weight, preferably greater than 30% by weight and preferentially greater than 35% by weight relative to the total weight of the composition.

A composition according to the invention may also comprise at least one glycol containing from 2 to 8 carbon atoms, such as glycerol, propylene glycol, butylene glycol and pentylene glycol, preferably glycerol.

Such a glycol may be present in the composition in a concentration of less than 10% by weight and preferably less than 5% by weight relative to the total weight of the composition.

A composition according to the invention may also comprise ingredients commonly used in cosmetics and more especially in the cosmetic and/or nailcare field.

They may be chosen in particular from film-forming polymers, plasticizers, pigments, nacres and dyes.

For the purpose of the present invention, the term "film-forming polymer" denotes a polymer that is capable, by itself or in the presence of a plasticizer, of forming an isolable and in particular continuous and adherent film, on a substrate, in particular on the nails.

A single film-forming polymer or a mixture of film-forming polymers may be used in the composition.

This film-forming polymer may be chosen from the group formed by synthetic polymers, of radical type or of polycondensate type, and polymers of natural origin, and mixtures thereof.

A film-forming polymer that is suitable for use in the invention may be chosen in particular from:

polysaccharides. Among the polysaccharides that are suitable for use in the invention, examples that may be mentioned include cellulose esters and ethers, such as nitrocellulose, cellulose acetate, cellulose acetobutyrate, cellulose acetopropionate and ethylcellulose, or alternatively optionally modified guar gum, such as ethylguar;

silicone resins. The nomenclature of silicone resins is known under the name "MDTQ", the resin being described as a function of the various siloxane monomer units it comprises, each of the letters M, D, T and Q characterizing a type of unit. By way of examples, mention may be made of polymethylsilsesquioxane resins, sold in particular by the company Wacker under the reference Resin MK, such as Belsil PMS MK, or by the company Shin-Etsu under the reference KR-220L. Mention may also be made of polyphenylsilsesquioxane resins, sold in particular by the company Wacker under the reference Belsil SPR 45VP. Mention may also be made of trimethyl siloxysilicate (TMS) resins such as those sold under the reference SR 1000 by the company General Electric or under the reference TMS 803 by the company Wacker;

synthetic polymers such as polyurethanes, acrylic polymers, vinyl polymers, polyvinyl butyrals, alkyd resins and ketone/aldehyde resins, resins derived from aldehyde condensation products, such as arylsulfonamide-formaldehyde resins, for instance toluenesulfonamide-formaldehyde resin, arylsulfonamide-epoxy resins or ethyl tosylamide resins;

polymers of natural origin, such as plant resins, such as dammar resins, elemi gum, copal resins, and benzoin; gums such as shellac, sandarac gum and gum mastic.

Use may in particular be made, as film-forming polymer, of the toluenesulfonamide/formaldehyde resins Ketjentflex MS80 from Akzo or Santolite MHP or Santolite MS 80 from Faconnier or Resimpol 80 from Pan Americana, the alkyd resin Beckosol ODE 230-70-E from Dainippon, the acrylic resin Acryloid B66 from Röhm & Haas, the polyurethane resin Trixene PR 4127 from Baxenden or the acetophenone/formaldehyde resin sold under the reference Synthetic Resin SK by Degussa.

According to one particular embodiment, the film-forming polymer is chosen from polysaccharides or polysaccharide derivatives, preferably from cellulose ethers and esters.

According to another particular embodiment, the film-forming polymer is chosen from silicone resins, preferably from polysilsesquioxanes.

For example, the content of film-forming polymer may range from 0.1% to 30% by weight, especially from 0.5% to 20% by weight and in particular from 1% to 10% by weight relative to the total weight of the composition.

The plasticizer may be chosen from any compound known to those skilled in the art as being capable of satisfying the desired function, and may be chosen in particular from plasticizers for the film-forming polymer.

In particular, mention may be made, alone or as mixtures, of the usual plasticizers, such as:

glycol derivatives such as diethylene glycol ethyl ether, diethylene glycol methyl ether, diethylene glycol butyl ether or else diethylene glycol hexyl ether, ethylene glycol ethyl ether, ethylene glycol butyl ether and ethylene glycol hexyl ether, glycol esters, propylene glycol derivatives and in particular propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether, diethylene glycol methyl ether and propylene glycol butyl ether, fatty alcohols that are liquid at ambient temperature, with a branched and/or unsaturated carbon-based chain containing from 12 to 26 carbon atoms, for instance 2-octyldodecanol, isostearyl alcohol, oleyl alcohol, 2-hexyldecanol, 2butyloctanol and 2-undecylpentadecanol, higher fatty acids such as oleic acid, linoleic acid or linolenic acid, and mixtures thereof, esters of acids, in particular carboxylic acids, such as the monoesters of formula $R_1COOR_2$ in which $R_1$ represents the residue of a linear or branched acid containing from 1 to 40 carbon atoms and $R_2$ represents a hydrocarbon-based chain, which is in particular branched, containing from 1 to 40 carbon atoms, provided that $R_1+R_2$ is >10, triglycerides consisting of fatty acid esters of glycerol, the fatty acids of which can have varied chain lengths of from $C_4$ to $C_{24}$, citrates, in particular triethyl citrate, tributyl citrate, triethyl acetylcitrate, tributyl acetylcitrate, 2-triethylhexyl acetylcitrate; phthalates, in particular diethyl phthalate, dibutyl phthalate, dioctyl phthalate, dipentyl phthalate, dimethoxyéthyl phthalate; trimellitates such as, in particular, tris-2-ethylhexyl trimellitate, L7,9-trimellitate, L8,10-trimellitate; phosphates, in particular tricresyl phosphate, tributyl phosphate, triphenyl phosphate, tributoxyethyl phosphate; tartrates, in particular dibutyl tartrate; adipates, such as, in particular, diethyl adipate and diisobutyl adipate; carbonates; sebacates; benzyl benzoate, butyl acetylricinoleate, glyceryl acetylricinoleate, butyl glycolate, glyceryl triacetate, plasticizers of polyester type, camphor, N-ethyl-o,p-toluenesulfonamide, oxyethylenated derivatives such as oxyethylenated oils, in particular vegetable oils such as castor oil, linear or branched hydrocarbons of mineral or synthetic origin, such as petroleum jelly, polydecenes, hydrogenated polyisobutene such as Parleam®, and squalane, and mixtures thereof, and in particular hydrogenated polyisobutene, silicone oils. The silicone oils that can be used in the composition may be non-volatile polydimethylsiloxanes (PDMSs), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and dimethicones or phenyl trimethicones with a viscosity of less than or equal to 100 cSt, and mixtures thereof, and mixtures thereof.

The type and amount of plasticizer may be chosen by a person skilled in the art on the basis of his general knowledge.

For example, the plasticizer content may range from 0.01% to 10% and in particular from 1% to 5% by weight relative to the total weight of the composition.

A composition according to the invention may also comprise at least one organic or mineral colorant, in particular such as pigments or nacres conventionally used in cosmetic compositions.

The term "pigments" should be understood as meaning white or coloured, mineral or organic particles that are insoluble in an aqueous solution, which are intended to colour and/or opacify the resulting film.

The pigments may be present in a proportion of from 0.01% to 15% by weight, especially from 0.01% to 10% by weight and in particular from 0.02% to 5% by weight relative to the total weight of the composition. As inorganic pigments that may be used in the invention, mention may be made of titanium oxide, zirconium oxide or cerium oxide, and also zinc oxide, iron oxide or chromium oxide, ferric blue, manganese violet, ultramarine blue and chromium hydrate.

They may also be pigments having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

The colorant may also comprise a pigment with a structure that may be, for example, of silica microspheres containing iron oxide type. An example of a pigment having this structure is the product sold by the company Miyoshi under the reference PC Ball PC-LL-100 P, this pigment being constituted of silica microspheres containing yellow iron oxide.

Among the organic pigments that may be used in the invention, mention may be made of carbon black, pigments of D&C type, lakes based on cochineal carmine or on barium, strontium, calcium or aluminium, or alternatively the diketopyrrolopyrroles (DPPs) described in documents EP-A-542 669, EP-A-787 730, EP-A-787 731 and WO-A-96/08537.

According to one particular embodiment of the invention, the pigments may be treated or coated with a treatment agent.

The treatment agent may be chosen from alkoxysilanes, silicones such as methicones, dimethicones, and perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups, amino acids, N-acylamino acids or salts thereof; lecithin, isopropyl triisostearyl titanate, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be the aluminium, magnesium, calcium, zirconium, zinc, sodium or potassium salts. The amino acid may be, for example, lysine, glutamic acid or alanine.

The term "nacres" should be understood as meaning coloured particles of any form, which may or may not be iridescent, especially produced by certain molluscs in their shell, or alternatively synthesized, and which have a colour effect via optical interference.

The nacres may be chosen from nacreous pigments such as titanium mica coated with an iron oxide, mica coated with bismuth oxychloride, titanium mica coated with chromium oxide, titanium mica coated with an organic dye and also nacreous pigments based on bismuth oxychloride. They may also be mica particles at the surface of which are superimposed at least two successive layers of metal oxides and/or of organic colorants.

Examples of nacres that may also be mentioned include natural mica coated with titanium oxide, with iron oxide, with natural pigment or with bismuth oxychloride.

Among the commercially available nacres that may be mentioned are the nacres Timica, Flamenco and Duochrome (on mica base) sold by the company Engelhard, the Timiron nacres sold by the company Merck, the Prestige nacres on mica base sold by the company Eckart and the Sunshine nacres on synthetic mica base sold by the company Sun Chemical.

The nacres may more particularly have a yellow, pink, red, bronze, orangey, brown, gold and/or coppery colour or glint.

As illustrations of nacres that may be used in the context of the present invention, mention may be made especially of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

A composition according to the invention may also comprise water-soluble or liposoluble dyes in a content ranging from 0.01% to 10% by weight and especially ranging from 0.01% to 5% by weight relative to the total weight of the composition.

The liposoluble dyes are, for example, Sudan Red, DC Red 17, DC Green 6, β-carotene, soybean oil, Sudan Brown, DC Yellow 11, DC Violet 2, DC Orange 5 and quinoline yellow. The water-soluble dyes are, for example, beetroot juice or methylene blue.

It may also contain one or more formulation additives commonly used in cosmetics and more especially in the field of nail cosmetics. They may be chosen especially from vitamins, trace elements, softeners, sequestrants, wetting agents, thickeners, dispersants, antifoams, spreading agents, co-resins, film-forming polymers, plasticizers, fillers, coalescers, preservatives, UV-screening agents, active agents, moisturizers, neutralizers, stabilizers and antioxidants, and mixtures thereof.

A composition in accordance with the invention more particularly intended for making up and/or caring for the nails may especially comprise, as active agents, keratin material hardeners, active agents that act on nail growth, for instance methylsulfonylmethane, and/or active agents for treating various ailments located on the nail, for instance onychomycosis.

The amounts of these various ingredients are those conventionally used in this field, for example from 0.01% to 20% by weight and especially from 0.02% to 10% by weight relative to the total weight of the composition in accordance with the invention.

A composition according to the invention may be in the form of an aqueous, organic or aqueous-alcoholic solution or suspension, an oil-in-water, water-in-oil or multiple emulsion, especially a cream or a milk; an aqueous or oily gel, a dispersion, a spray composition or a patch.

A composition according to the invention may thus be in the form of a makeup composition such as a nail varnish, a varnish base, a nailcare product, a liquid lipstick, a foundation, a haircare composition such as a lacquer, a styling lotion or a styling spray.

It is more preferentially a nail varnish, said nail varnish possibly being transparent or coloured.

A composition according to the invention comprises a physiologically acceptable medium.

The term "physiologically acceptable medium" is intended to mean a non-toxic medium that may be applied to human keratin materials and that has a pleasant appearance, odour and feel.

Coating Kit

When the composition according to the present invention contains a mixture of alkoxysilane compounds, it can also be in the form of a kit for coating keratin materials comprising at least two different compositions packaged separately. Said kit may comprise the product resulting from the reaction of (a) and (b) as defined previously, and optionally the constituents (c) to (g) as defined previously.

According to one embodiment, on the one hand the product resulting from the reaction of (a) and (b), and, on the other hand, the alkoxysilane (d) are packaged in the same composition.

According to a second embodiment, on the one hand the product resulting from the reaction of (a) and (b), and, on the other hand, the alkoxysilane (d) are packaged in at least two different compositions, a first and a second composition.

According to this second embodiment, said at least two different compositions may be combined just before or during application.

Said first and/or second different compositions of the kit according to the invention may also comprise at least one additional compound as defined previously.

According to one embodiment, the first composition of the kit according to the invention, as defined previously, may also comprise at least one additional compound and/or the second composition of the kit according to the invention, as defined previously, may also comprise at least one such additional compound, which is identical to or different from that or those optionally present in the first composition.

Each composition of the kit may be packaged separately in the same packaging article.

According to one particular embodiment, each composition of the kit according to the invention may be packaged in a two-compartment pen, the first composition being delivered from one end of the pen and the second composition being delivered from the other end of the pen, each end being, for example, closed in a leaktight manner by a cap.

Each composition may also be packaged in a separate compartment within the same packaging article, the mixing of the at least two compositions taking place at the end(s) of the packaging article during the delivery of the composition. The packaging article(s) may be watertight and/or airtight.

Alternatively, each composition may be packaged in a different packaging article.

Furthermore, each composition is liquid before application to the keratin materials. Following the sol/gel reaction, a film is obtained directly on the keratin materials.

Coating Process

According to the embodiment relating to the single composition, the present invention relates to a cosmetic process for coating keratin materials which consists in applying to said keratin materials at least one coat of a composition in accordance with the invention.

According to the embodiment in kit form, the present invention also relates to a cosmetic process for coating keratin materials which consists in applying to said keratin materials at least one coat of a mixture of at least two different compositions as defined above.

According to one embodiment, the coating process according to the invention consists in extemporaneously mixing said at least two different compositions comprising, on the one hand, the product resulting from the reaction of (a) and (b), and, on the other hand, the compound (d), an alcohol and/or a cosmetic or dermatological active agent as defined previously, and in applying to said keratin materials at least one coat of said mixture obtained.

According to another embodiment, the coating process according to the invention consists in applying to the keratin materials at least one coat of a first composition and at least one coat of a second composition, said first and second compositions being different and together comprising the product resulting from the reaction of (a) and (b) and the compounds (c) to (g) as defined previously.

The order of application of said first and second different compositions is irrelevant.

It is also possible to alternately apply to the keratin materials several coats of each of said first and second different compositions.

Needless to say, each composition comprises a physiologically acceptable medium, i.e. a non-toxic medium, that may be applied to human keratin materials and that has a pleasant appearance, odour and feel.

According to one preferred embodiment, said keratin materials more particularly concern the nails.

According to one embodiment, the composition(s) and the mixture according to the invention may be applied to the keratin materials, and more particularly the nails, using a brush, or even several brushes in the case of the kit.

According to another embodiment, the composition(s) and the mixture according to the invention may be applied to the keratin materials, and more particularly the nails, using a felt-tip pen, or even several felt-tip pens in the case of the kit. Such pens are described, for example, in patent FR 2 909 844.

According to one particular embodiment, said coating process is performed with application of heat.

This application of heat, when the composition is a liquid lipstick, may be, for example, a means not specifically intended for heating, such as a hot body (hot cup or drink).

The composition may also be heated using a means specifically dedicated to heating, for instance a means for propelling hot air such as a hair dryer or a drying device, for instance a heating applicator.

The examples given below are presented as non-limiting illustrations of the invention.

In the following examples, the references of the raw materials used have been listed:

MTES (methyltriethoxysilane): Dynasylan MTES (Evonik)
APTES (3-aminopropyltriethoxysilane): Silsoft A-1100 (Momentive Performance Materials)
TEOS (tetraethoxysilane): Dynasylan TEOS UHP (Evonik)
N-cyclohexylaminomethyltriethoxysilane: Geniosil XL 926 (Wacker)
Acetoxymethyltriethoxysilane: AB110784 (ABCR)
Ethylcellulose: Ethocel Standard 45 Premium (DOW Chemical)

EXAMPLE 1

MTES/TEOS/APTES System

In a plastic flask, 7.37 g of a 0.1M aqueous HCl solution are added to a mixture of 16.22 g of MTES (M=178.3 g/mol) and 66.34 g of TEOS (M=208.33 g/mol). The alkoxysilane monomers and the 0.1 M HCl solution are stirred vigorously using a magnetic stirrer until a clear solution is obtained. 10 minutes after the solution becomes clear, 10.07 g of APTES (M=221.37 g/mol) are added to the mixture. After one hour of stirring, the solution is placed in an incubator at 60° C. for 24 h. The solution is then diluted with 175 g of absolute ethanol.

$n_{H2O}$=0.41

$$X=(n_{Alkoxysilanes} \times nb_{Alkoxy\ groups})/n_{H2O}=4.11$$

Films are spread on a contrast card. After 10 to 15 min, a shiny transparent film is obtained. The final solution does not gel over time.

EXAMPLE 2

MTES/TEOS/APTES System+Ethylcellulose

In a plastic flask, 7.37 g of 0.1 M HCl are added to a mixture of 16.22 g of MTES and 66.34 g of TEOS. The alkoxysilane monomers and the 0.1 M HCl solution are stirred vigorously using a magnetic stirrer until a clear solution is obtained. 10 minutes after the solution becomes clear, 10.07 g of APTES are added to the mixture. After one hour of stirring, the solution is placed in an incubator at 60° C. for 24 h. A mixture of 55 g of ethylcellulose (Ethocell Standard 45 Premium from Dow Chemical), 55 g of ethyl acetate and 110 g of absolute ethanol are then added to the alkoxysilane solution at ambient temperature.

$n_{H2O}$=0.41

$$X=(n_{Alkoxysilanes} \times nb_{Alkoxy\ groups})/n_{H2O}=4.11$$

Films are spread on a contrast card. After 10 to 15 min, a shiny transparent film is obtained. The final solution does not gel over time.

EXAMPLE 3

N-Cyclohexylaminomethyltriethoxysilane Homooligomer System

In a plastic flask, 6.13 g of ultrapure water are added to 93.87 g of N-cyclohexylaminomethyltriethoxysilane (M=275.46 g/mol). The alkoxysilane monomers and the ultrapure water are stirred vigorously using a magnetic stirrer. After one hour of stirring, the solution is placed in an incubator at 60° C. for 24 h.

$n_{H2O}=0.34$ $$X=(n_{Alkoxysilanes} \times nb_{Alkoxy\ groups})/n_{H2O}=3$$

Films are spread on a contrast card. After 15 to 20 min, a shiny transparent film is obtained. The final solution does not gel over time.

EXAMPLE 4

MTES/Acetoxymethyltriethoxysilane/APTES System

In a plastic flask, 7.85 g of 0.1 M HCl are added to 69.1 g of MTES. The alkoxysilane monomers and the 0.1 M HCl solution are stirred vigorously using a magnetic stirrer until a clear solution is obtained. 10 minutes after the solution becomes clear, 11.45 g of acetoxymethyltriethoxysilane (M=236.34 g/mol), 10.72 g of APTES and 0.87 g of pure water are added to the mixture. After one hour of stirring, the solution is placed in an incubator at 60° C. for 24 h.

$n_{H2O}=0.48$ $$X=(n_{Alkoxysilanes} \times nb_{Alkoxy\ groups})/n_{H2O}=3$$

Films are spread on a contrast card. After 15 to 20 min, a shiny transparent film is obtained. The final solution does not gel over time.

EXAMPLE 5

(Comparative): MTES/APTES System

In a plastic flask, 24.99 g of 0.1 M HCl are added to a mixture of 61.89 g of MTES. The alkoxysilane monomers and the 0.1 M HCl solution are stirred vigorously using a magnetic stirrer until a clear solution is obtained. 10 minutes after the solution becomes clear, 25.61 g of APTES are added to the mixture.

$n_{H2O}=1.39$
$X=1$

After stirring for 30 minutes, the solution is gelled.

The invention claimed is:

1. A cosmetic or dermatological sol/gel composition remaining in liquid form before application to keratin materials, the composition comprising a product resulting from the reaction:
   (a) of 3-aminopropyltriethoxysilane (APTES) with methyltriethoxysilane (MTES), and
   (b) of an amount of water corresponding to a number of moles of water, determined according to the following equation:

$$X=(n_{Alkoxysilanes} \times nb_{Alkoxy\ groups})/n_{H2O}$$

with:
   $n_{H2O}$=Number of moles of water,
   $n_{Alkoxysilanes}$=Number of moles of alkoxysilane compounds,
   $nb_{Alkoxy\ groups}$=Weighted mean of the number of alkoxysilane groups per alkoxysilane compound,
   and X is a number of 3-4.11.

2. The composition of claim 1, further comprising at least one member selected from the group consisting of (c), (e), (f) and (g):
   (c) an acid and/or a base;
   (e) a film-forming polymer;
   (f) a reactive additive comprising a hydroxyl function; and
   (g) a solvent or a mixture of solvents.

3. The composition of claim 2, comprising more than 25% by weight of the sum of the product resulting from the reaction of (a) and (b), and of the optional compounds (c) and (e).

4. The composition of claim 1, further comprising at least one cosmetic or dermatological active agent selected from the group consisting of film-forming polymers, plasticizers, pigments, nacres, dyes, vitamins, trace elements, softeners, sequestrants, wetting agents, thickeners, dispersants, antifoams, spreading agents, co-resins, plasticizers, fillers, coalescers, preserving agents, UV-screening agents, active agents, moisturizers, neutralizers, stabilizers and antioxidants.

5. The composition of claim 1, which is a nail varnish, a varnish base, a nailcare product, a liquid lipstick, a foundation, or a haircare composition.

6. A cosmetic process for coating a keratin materials material, comprising applying to said keratin material at least one coat of the cosmetic composition of claim 1.

* * * * *